US00PP35429P2

(12) United States Plant Patent
Hansen

(10) Patent No.: US PP35,429 P2
(45) Date of Patent: Oct. 17, 2023

(54) ***HEUCHERA* PLANT NAMED 'BALL GOWN'**

(50) Latin Name: ***Heuchera* hybrid**
Varietal Denomination: Ball Gown

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 29 days.

(21) Appl. No.: 17/803,769

(22) Filed: Nov. 16, 2022

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 6/80
See application file for complete search history.

(56) References Cited

U.S. PATENT DOCUMENTS

PP16,735 P2 * 6/2006 Egger ..... A01H 6/80 Plt./440
PP29,361 P2 * 6/2018 Hansen ..... A01H 5/12 Plt./440

* cited by examiner

*Primary Examiner* — June Hwu

(57) ABSTRACT

The new and distinct hybrid of *Heuchera* plant named 'Ball Gown' with large-sized, ruffled, chartreuse foliage. The new plant has creamy white flowers on dense panicles that repeat through the growing season. The new plant is vigorous, and produces dense clumps and is useful in the landscape or in containers.

2 Drawing Sheets

Botanical denomination: *Heuchera* hybrid.
Variety denomination: 'Ball Gown'.

STATEMENT REGARDING PRIOR DISCLOSURES UNDER 37 CFR 1.77(B)(6)

The first public information of the claimed plant, in the form of a non-enabling photograph and brief description, was on a website operated by Walters Gardens, Inc. first accessible on Dec. 1, 2021. This was followed by a small photograph and brief description in the "Walters Gardens 2022-2023 Catalog" first distributed on Jun. 8, 2022. Walters Gardens, Inc. obtained the new plant and all information about the new plant from the inventor. No plants of *Heuchera* 'Ball Gown' have been sold in this country or anywhere in the world, nor has any disclosure of the new plant been made, more than one year prior to the filing date of this application, and such sale or disclosure within one year was either derived directly or indirectly from the inventor and thus should be considered a 35 U.S.C. § 102(b) exception.

BACKGROUND OF THE INVENTION

The present invention relates to a new and distinct cultivar of Coral Bells in the Saxifragaceae family and given the cultivar name of 'Ball Gown'. *Heuchera* 'Ball Gown' was hybridized by the inventor on Mar. 20, 2015, in the greenhouses of a wholesale perennial nursery in Zeeland, Mich., USA and initially assigned the breeder code 15-176-9. The seed or female parent was the proprietary, unreleased, unnamed seedling known only by the breeder code 13-486-19 (not patented) and the pollen or male parent was the proprietary, unreleased, unnamed seedling known only by the breeder code 13-764-1 (not patented). The female parent is a cross comprising 'Mocha' U.S. Plant Pat. No. 18,386, 'Tnheu042' also known as 'Key Lime Pie' U.S. Plant Pat. No. 16,735 and 'Pistache' U.S. Plant Pat. No. 19,585. The male parent comprised ancestry of 'Cajun Fire' U.S. Plant Pat. No. 24,150, 'Mocha', and other proprietary non-patented hybrids and selections.

*Heuchera* 'Ball Gown' was first selected in the fall of 2016 and passed final evaluation in the fall of 2020 from among hundreds of other seedlings from the same cross and hundreds of other crosses. *Heuchera* 'Ball Gown' has been asexually propagated by division at the same nursery in Zeeland, Mich. in 2016 and by careful shoot tip tissue culture propagation. The resultant asexually propagated plants have remained stable and continued to exhibit the same characteristics as the original plant for multiple generations.

BRIEF SUMMARY OF THE INVENTION

The female parent has chartreuse leaves that are smaller and more tightly ruffled with more leaves per clump. The male parent has pinkish flowers and larger, less ruffled foliage that are more bronze in color.

The nearest comparison cultivars known to the inventor include: 'Pistache', 'Pretty Pistachio' U.S. Plant Pat. No. 29,361, 'Electric Lime' U.S. Plant Pat. No. 21,872, 'Lime Marmalade' U.S. Plant Pat. No. 21,861, and 'Pistachio Ambrosia' U.S. Plant patent application Ser. No. 17/803,768.

'Key Lime Pie' has a smaller habit with smaller foliage and slightly more rounded leaf apices and lobes are closer together, and the flowers have a more pinkish effect. 'Mocha' has a larger habit, flatter foliage of bronze purple with royal purple undersides and the flowers are cream-colored. 'Cajun Fire' has large reddish foliage with ruffles and smaller creamy-white flowers on less dense panicles.

'Pistache' has flatter foliage and more open panicles of creamy flowers. 'Pretty Pistachio' has slightly smaller and flatter foliage that is more prone to sun damage, and the flowers are more pinkish. 'Pistachio Ambrosia' has more rounded and shallowly lobed leaves with pinkish flower effect and the foliage is more resistant to sun damage. 'Electric Lime' has smaller foliage with light green foliage and contrasting blood-red veins in cool temperatures, and smaller cream-colored flowers. 'Lime Marmalade' has smaller more ruffled and deeply incised foliage with more airy panicles of smaller flowers.

*Heuchera* 'Ball Gown' differs from its parents as well as all other coral bells known to the applicant in the following combined traits:

1. Large-sized cordate leaf blades are light chartreuse in the spring becoming darker chartreuse in summer with both surfaces matte;
2. Produces creamy-white flowers begin in early summer and lasting for about four weeks repeating until frost;
3. Panicles are densely-branched with flowers and rise just above foliage;
4. Produces dense clumps and many large individual leaves;
5. Plant is moderately vigorous.

BRIEF DESCRIPTION OF THE DRAWINGS

The photographs of the new plant demonstrate the overall appearance of the plant including the unique traits. The colors are as accurate as reasonably possible with modern color reproductions. Some slight variations of color may occur as a result of lighting quality, intensity, wavelength, and direction or reflection.

DETAILED BOTANICAL DESCRIPTION

Figure 1:
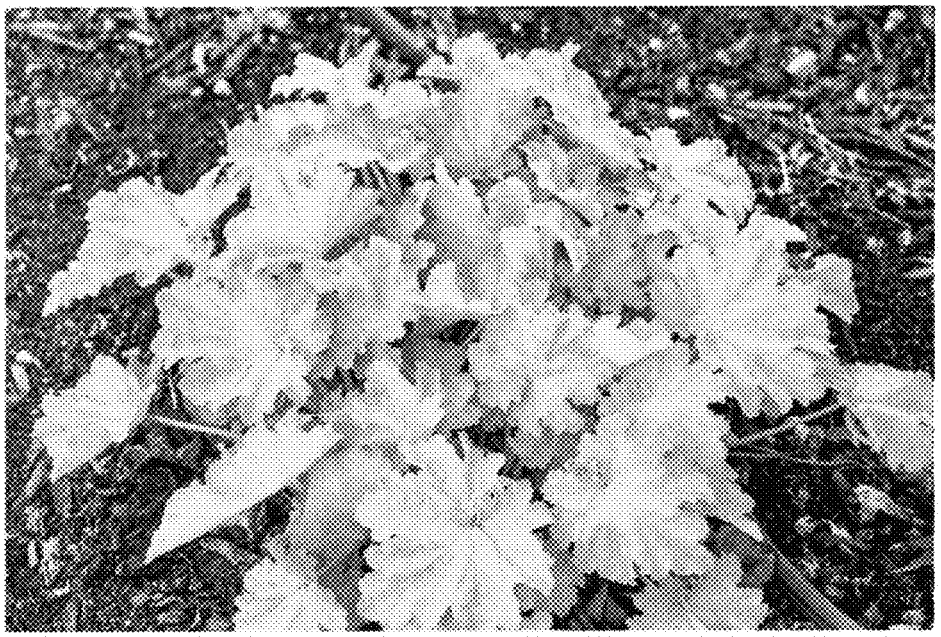
FIG. 1 shows a two-year-old plant in a partially shaded garden prior to flowering in spring.
Figure 2:
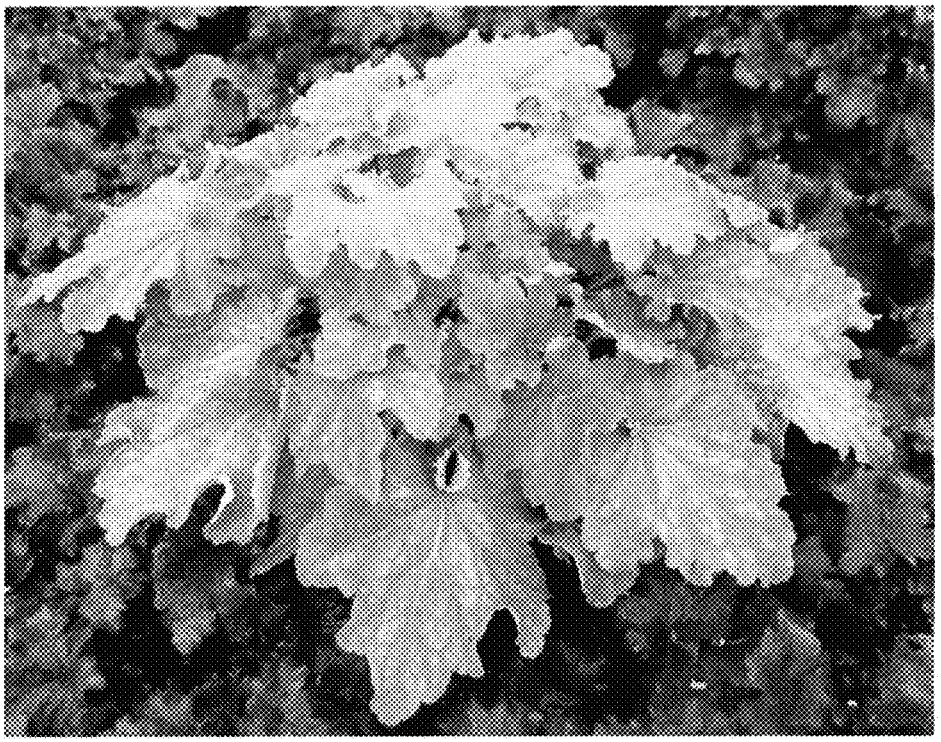
FIG. 2 shows a one-year-old plant in a partially shaded garden mid-season.
Figure 3:
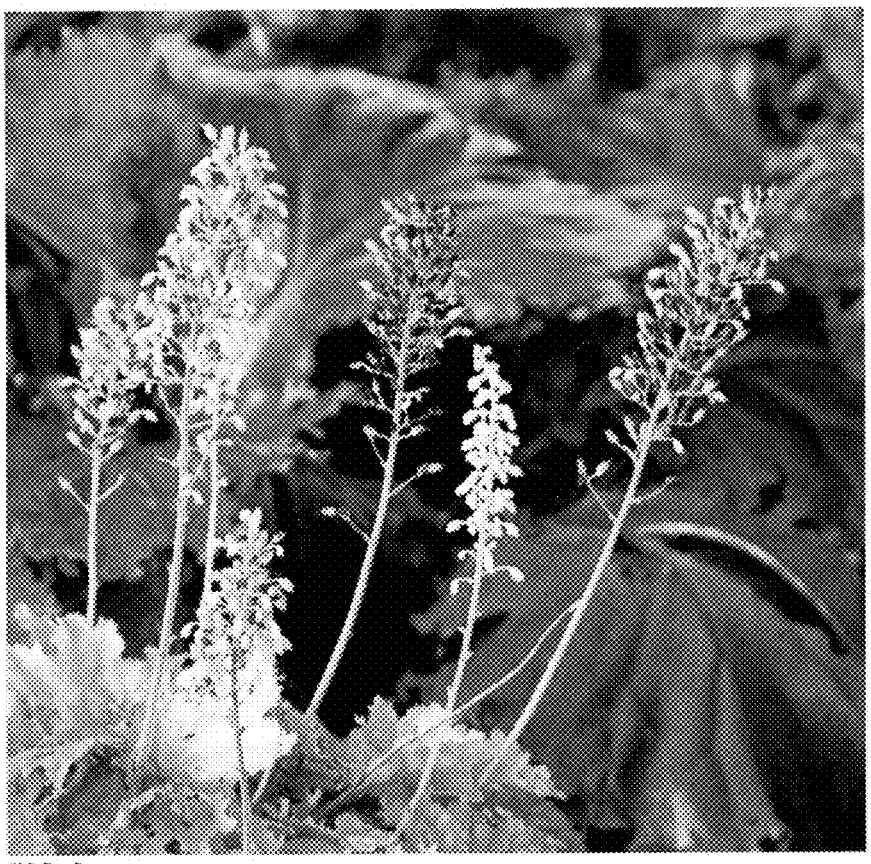
FIG. 3 shows a close-up of the new and repeating inflorescences showing flowers and buds.

The following description is based on one-year-old plants of 'Ball Gown' grown in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the unreleased hybrid 13-486-19 and the pollen or male parent was the unreleased hybrid 13-764-1;

Plant habit: Hardy herbaceous perennial with basal rosette of foliage; mounded foliage to about 24 cm tall and 60 cm in diameter with upright scapes to about 36 cm long; stems to about 36 cm long and 4 mm diameter at base, with about 10 to 16 leaves per stem and 8 main stems per plant;

Roots: Fibrous, finely branched;

Growth rate: Rapid, rooting from cutting in two weeks and finishing in a three-liter container in about 3 months;

Foliage: Cordate; sparsely hirsutulous adaxial and abaxial; palmately shallowly lobed with five to seven main lobes shallowly dissected less than one-quarter the way to petiole or midrib with four to six main indentations and numerous minor indentations; apex and lobes rounded to apiculate, base cordate to auriculate with basal lobes frequently overlapping about 1.5 cm; margins crenate to mucronate, ciliolate; slightly lustrous adaxial becoming matte adaxial, and matte abaxial; held nearly horizontal; marginal undulation moderate;

Leaf blade size: to about 140 mm long and 130 mm wide, average about 105 mm long and 95 mm wide;

Leaf color: spring and young emerging leaves adaxial nearest RHS 145A to between RHS 145A and RHS 146D, with no silver. or dark green marbling surrounding the veins, spring young emerging leaves abaxial between RHS 145C and RHS 193A; mature mid-season leaves adaxial variable with some leaves with portions nearest RHS 145A, and patches of nearest RHS 145C between the veins, abaxial mature mid-season leaves between RHS 148D and RHS 148C; late season adaxial nearest RHS 146C with lighter patches of nearest RHS 145D, abaxial nearest RHS 194B; deciduous with no winter color;

Leaf quantity: Dense, about 130 per plant;

Veins: Palmate; micro-puberulent adaxial and hirsutulous to pubescent abaxial; nearly flat adaxial and costate abaxial;

Vein color: On emerging or early spring foliage adaxial nearest RHS 145B with emerging or early spring abaxial primary veins nearest RHS 145D and secondary veins nearest RHS 146D; mid-season and flowering time adaxial nearest RHS 145C proximally and nearest RHS 145A distally, midseason and flowering time abaxial primary veins nearest RHS 145C and secondary veins between RHS 146D and RHS 145A; late season adaxial nearest RHS 146D and abaxial primary veins nearest 148C proximally and distal primary and secondary veins nearest RHS 146B;

Petiole: Terete; pubescent with hairs to about 2 mm long; with base amplexicaul; to about 17.5 cm long and 4.5 mm diameter just above stipule; average about 15 cm long and about 4 mm diameter above stipule and 14 mm across at base including stipule;

Petiole color: Emerging leaf nearest RHS 145C; mature leaf nearest RHS 146C;

Stipule: At base of petiole, about 17 mm long and about 14 cm wide at base; with an acute apex on both sides; truncate base; ciliolate margin;

Stipule color: Adaxial and abaxial between RHS 150D and RHS 145D with faint blush of nearest RHS 186A;

Peduncle: To about 12 per plant throughout the growing season; panicle; terete; stiff; pubescent; upright; to about 36 cm long and 4 mm diameter at base, average about 30 cm tall and about 3 mm diameter; about 12 per plant with up to 130 flowers per panicle, average about 100; densely-branched panicle with up to 34 branches per peduncle up to about 2 cm long and about 1 mm diameter decreasing distally, average 20 branches per panicle; branches outwardly to slightly upright;

Inflorescence: Flower density high; flowering in upper 10 cm to about 3.8 cm wide;

Flowering longevity: Panicle effective for about four weeks; with new scapes emerging until frost; individual flowers lasting about 4 days on plant or as cut flower; persistent;

Peduncle color: Mature lower portion between RHS 145A and RHS 146D and distally between RHS 146D and RHS 151D;

Pedicel: Terete; finely puberulent; to about 6 mm long and 0.5 mm diameter, average about 4 mm long and 0.5 mm diameter; aspect outwardly to slightly drooping;

Pedicel color: Nearest RHS 145D with light blush of nearest RHS 182B;

Buds one day prior to opening: Ellipsoid; rounded apex and attenuate base; puberulent to glandular; about 5 mm long and 3 mm diameter;

Bud color one day prior to opening: Middle portion nearest RHS 145D and proximal and distal portions nearest RHS N144D;

Flower: Perfect; complete; campanulate; actinomorphic; about 7 mm long to exserted style and 3.5 mm in diameter at face;

Flower aspect: Slightly downwardly to outwardly;

Calyx: Base fused in proximal 4 mm to form hypanthium; pubescent abaxial; glabrous adaxial; about 6 mm long and 3.5 mm wide; persistent;

Sepal: Five; apex acute; fused in basal 4 mm and 2 mm wide at fusion; free in distal 2 mm; margins entire;

Sepal color: Adaxial proximally nearest RHS 150D, distally between RHS 146D and RHS 145A; abaxial proximally between RHS 157A and RHS 145C and distally nearest RHS 146D;

Petals: Five; spatulate; acute apex and attenuate base; margin entire, glabrous abaxial and adaxial; about 3 mm long and 1 mm wide about two-thirds of the way to apex;

Petal color: Abaxial and adaxial nearest RHS NN155D;

Androecium: Five; adnate to adaxial calyx about 2 mm above base;

*Filaments*.—Five, thin, glabrous; about 3.5 mm long and less than 0.3 mm diameter; color nearest RHS NN155D.

*Anthers*.—Ellipsoidal; distinct; basifixed; longitudinal; about 0.7 mm long and 0.5 mm across; color nearest RHS 23B.

*Pollen*.—Abundant; color nearest RHS N25C.

Gynoecium: One; two-beaked; half-inferior; bifid style with split at ovary; 6 mm long;

*Style*.—Bifid; split apart at apex of ovary; about 3.5 mm long and about 1 mm diameter near base; color nearest RHS 145D proximally and distally nearest RHS 155C.

*Stigma*.—Acute apex; about 0.1 mm diameter; color nearest RHS NN155B;

*Ovary*.—Half-inferior; about 2.5 mm long and 2 mm diameter; ellipsoidal to globose; base rounded; color nearest RHS 145C.

Fruit: Two-beaked ellipsoidal capsule; about 4 mm long and 2.5 mm across; color nearest RHS 200B;

Seed: Not yet been observed;

Growth: The new plant grows best with ample moisture and drainage in either part sun or shade and is winter hardy from USDA zones 4 to 9.

Disease and pest tolerance: Resistance and tolerance outside of that normal for *Heuchera* has not been observed.

It is claimed:

1. A new and distinct coral bells plant named *Heuchera* 'Ball Gown' as herein described and illustrated.

* * * * *